| United States Patent [19] | [11] Patent Number: 4,872,987 |
| Kopsch et al. | [45] Date of Patent: Oct. 10, 1989 |

[54] PROCESS FOR SEPARATING AND PRODUCING CHLOROGENIC ACID

[75] Inventors: Reiner Kopsch, Schenefeld; Claus F. Gösswein, Buchholz; Henning Lutz; Michael Ball, both of Halstenbek; Peter Hubert, Buxtehude, all of Fed. Rep. of Germany

[73] Assignee: Ergo Forschungsgesellschaft mbH, Hamburg, Fed. Rep. of Germany

[21] Appl. No.: 326,488

[22] Filed: Mar. 20, 1989

Related U.S. Application Data

[63] Continuation of Ser. No. 131,191, filed as PCT EP87/00049 on Feb. 3, 1987, published as WO87/04704 on Aug. 13, 1987, abandoned.

[30] Foreign Application Priority Data

Feb. 6, 1986 [DE] Fed. Rep. of Germany ....... 3603574

[51] Int. Cl.$^4$ ............................................. B01D 15/08
[52] U.S. Cl. .................................. 210/635; 210/656; 426/422
[58] Field of Search ............ 210/635, 656, 659, 198.2; 426/422

[56] References Cited

U.S. PATENT DOCUMENTS

| 3,502,545 | 3/1970 | Westman | 210/635 |
| 3,664,845 | 5/1972 | Friedman | 210/635 |
| 4,113,887 | 9/1978 | Keamer | 426/422 |
| 4,113,888 | 9/1978 | Henig | 426/422 |
| 4,130,556 | 12/1978 | Wachter | 210/635 |
| 4,278,696 | 7/1981 | Magnolato | 426/422 |
| 4,426,292 | 1/1984 | Wernick | 210/635 |
| 4,714,555 | 12/1987 | Shibata | 210/635 |

OTHER PUBLICATIONS

Laffanzio, Determination of Plant Phenol by Gel Filtration, Journal of Food Science, vol. 46, (1981), pp. 1907-1909 and 1917.

Mikes' Laboratory Handbook of Chromatographic and Allied Methods, Ellis Horwod Limited, 1979, pp. 399 & 370.

Snyder, Introduction to Modern Liquid Chromatography, Second Editions, 1979, John Wiley & Sons, p. 723.

The Merck Index, Tenth Edition, Merck & Co., 1983, p. 217.

*Primary Examiner*—Ernest G. Therkorn
*Attorney, Agent, or Firm*—Cushman, Darby & Cushman

[57] ABSTRACT

Chlorogenic acid can be separated and produced as free acid or as salts thereof from plant raw material extracts by means of gel permeation chromatography on cross-linked modified polysaccharides, especially on dextrans. To obtain the free acid, the aqueous extract must be adjusted to a pH in the range of about 2 to 2.8. By use of a column of sufficient length the isomeric 5-, 4- and 3-chlorogenic acid can also be separated by the process of the invention.

8 Claims, 4 Drawing Sheets

Separation of chlorogenic acid from raw coffee extract at pH 2,5 and 5,6 on SEPHADEX® G 25, 15 and 10

FIG. 2  Isolation of chlorogenic acid from bilberry leaves on SEPHADEX R
Depiction of separation mode: HPLC fractograms FIG. 3 Purification of chlorogenic acid from bilberry leaves on SEPHADEX® G15. Determination of purity of chlorogenic acid in dependence on the elution volume; HPLC-Peak images of 10mg dry substance in 100 ml $H_2O$

PROCESS FOR SEPARATING AND PRODUCING CHLOROGENIC ACID

This is a continuation of application Ser. No. 131,191, filed as PCT EP87/00049 on Feb. 3, 1987, published as WO87/04704 on Aug. 13, 1987, now abandoned.

The invention relates to a simplified process for the separation and production of chlorogenic aicd by aqueous extraction of suitable plant raw materials and processing of the extract.

K. Gorter, Liebigs Ann. 358, 237–348 (1908), K. Freudenberg, Ber. 53, 232–239 (1920) and also W. Pluml/u/ cker and W. Keilholz, Z. Lebensmittelunters. u. Forsch. 66, 200238 (1933) described processes for the preparation of chlorgenic acid. In all the known processes, the first step is the preparation of a potassium-caffeine-chlorogenate complex. This is purified by different methods, for example, by repeated recrystallization from ethanol/water or by precipitation with lead acetate. The caffeine can be separated from the purified complex, for example, by extraction of the aqueous solution with chloroform. The chlorogenic acid is then precipitated by the addition of sulphuric acid and further purified by recrystallization from water. The yield of chlorgenic acid is stated as 1%, based on the quantity of raw coffee used, corresponding to a yield of about 20%, based on the quantity of chlorogenic acid contained in the raw coffee.

Other process for the preparation of chlorgenic acid are based on a modification or combination of the earlier processes. For example, in Arzneimittelforschung 4, 41–45 (1954) U. Fiedler describes a process which is a combination of the methods of Freudenberg on the one hand and of Pluml/u/ cker and Keilholz on the other. In this method green coffee beans are dried and comminuted and then extracted first with petroleum ether and next with hot water, until the extracts contain no more chlorgenic acid. The combined extracts are concentrated and precipitated with barium acetate. Then the filtrate is precisely neutralized with sulphuric acid, the excess barium being removed at the same time. The chlorogenic acid is separated from the neutral filtrate by means of lead acetate as a complex, which is washed with hot water and to which hydrogen sulphide is then added after suspension in hot water. After standing in a refrigerator for two to three days, the potassium-caffeine-chlorogenate complex separates from the concentrated filtrate. Caffeine is removed from the complex by chloroform and then the free chlorogenic acid is obtained by weak acidification.

Chemical Abstracts 73, 32171E (1970) describes a process wherein the isomeric chlorogenic acids are eluated by column chromatography on silicic acids and elution with a chloroform-butanol gradient. Chemical Abstracts 89, 88927D (1978) discloses the extraction of chlorogenic acid from an aqueous extract of green coffee beans by anion exchangers such as Dowex 44, Amberlite IRA 410 or IRA 47 and Dowex 11.

Clearly, the known processes are very laborious and unable to give high yields. As far as chlorogenic acid is commercially available at all, it is therefore extremely expensive. Moreover, only 3-chlorogenic acid and the isomer mixture are available; hitherto no usable process has been known for the economic preparation of 4- or 5-chlorogenic acid. The expresson "3-chlorogenic acid" refers to the 3-caffeoyl-chinic acid and is used in this meaning hereinafter.

Also the isomers presently refered to as 4- and 5-chlorogenic acid signify the corresponding 4- and 5-caffeoyl-chinic acids.

It is therefore object of the invention to develop a simplified process for the separation and production of free chlorogenic acid or salts thereof in commercial scale amounts, which requires no toxicologically undesirable auxiliary chemicals. Further the process allows separation into the 3 isomers if required.

The invention relates to a process for the separation and preparation of chlorogenic acid by extracting suitable plant raw materials (i.e. such which contain an adequate quantity of chlorgenic acid) and processing the extract, the process being characterized in that the chlorogenic acid is separted from the extract by gel permeation chromatography on a molecular sieve of a cross-linked modified polysaccharide and especially a dextran and the chlorogenic acid and/or the extract free from chlorogenic acid are obtained.

Generally gel permeation chromatography on cross-linked dextrans is used for separating mixtures of substances by molecule size, i.e. the molecules appear in the eluate in the order of decreasing molecule size. In such separation of an aqueous plant extract containing chlorogenic acid a man skilled in the art would therefore expect that the chlorogenic acid would appear substantially in the center of the elution spectrum accompanied by a series of substances of the same or similar molecular weight. However, it was surprisingly found that on a molecular sieve of especially dextran gel chlorogenic acid does not behave in accordance with its molecular weight. It was discovered according to the invention that cross-linked modified polysaccharides and especially dextrans have a selective retention capacity for chlorogenic acid—i.e. chlorogenic acid is retained substantially longer than would be expected for its molecule size.

Unexpectedly the total quantity of the substances contained in the plant extract and having higher and lower molecular weight as chlorogenic acid emerge from the column in a broad fraction and the chlorogenic acid is selectively retained. By further elution it can be obtained in a relatively pure and distinctly separated fraction.

A particularly suitable material for separation is gels of cross-linked dextrans, such as those available under the name SEPHADEX ® According to the invention it has been found that the separation capacity rises with an increasing degree of cross-linkage of the dextran gel used—i.e., for a given column length a better separation is achieved with a dextran gel of higher cross-linkage than if gel with lower cross-linkage is used.

Regarding the degree of cross-linkage in a gel the swelling capacity of the same may be used as an indicator. The swelling capacity decreases with an inreasing number of cross-linkages. For instance 20 g of dry material of SEPHADEX ® G25 are necessary to obtain 100 ml of a swollen gel while 40 g of SEPHADEX ® G10 which is cross-linked to a substantially higher degree are necessary to obtain the same gel volume.

The suitable working temperature for separation is in the range of 10° to 80° C., room temperature being normally preferred. As a rule aqueous plant extracts are used for separation. The elution medium can therefore consist exclusively of water, but also of a mixture of water and e.g. alcohols. By selection of the solvent mixture the polarity of the solvent system may be influenced according to the respective requirements.

According to the invention the term "chlorogenic acid" covers both the free acid and also the salts of the same. With pH values such as are set up in aqueous plant extracts the chlorogenic acid should mainly be present in the form of its salt. For example, the pH of an aqueous extract of bilberry leaves is about 3.8, that of raw coffee extract being about 5.5. If substantially free chlorogenic acid is to be prepared by the process of the invention, the pH of the extract must be reduced accordingly. It was found that free chlorogenic acid can be separated readily and in a relatively pure form preferably by cross-linked dextrans, if the pH of the plant extract is brought to about 2 to about 2.8. It is not important which acid is added to lower the pH value. Mineral acids such as hydrochloric acid and sulphuric acid have been found to be particularly suitable. For certain purposes it may be more favourable to adjust the necessary acid pH value without the addition of acid. This can be done by extracting the cations from the extract solution using an ion exchanger.

A particularly good separation is achieved if at least two dextran gels are used which are cross-linked to different degrees; that part of the eluate of the first gel which contains the chlorogenic acid is then passed through the next gel. The gel with the lower degree of cross-linkage is used for the first separation. The dextran matrix with a higher number of cross-linkages and a lower swelling capacity (e.g., SEPHADEX® G 15) has according to the invention better separation characteristics than a type with less cross-linkages (e.g., SEPHADEX® G 25). However, these are not the only critical features for practical application. For instance the separation of viscous solutions requires a gel with favourable flow properties, a dextran with a lower degree of cross-linkages (such as SEPHADEX® G25) coarse being particularly suitable for this purpose.

It has also been found that by means of the process according to the above embodiment of the invention—i.e., also with about pH 2—the isomers of chlorogenic acid can in addition be separated if a long enough molecular sieve column is used, since in that case the isomeric 5-, 4- and 3-chlorogenic acids appear one after the other in the eluate and can be gathered separately. In this way substantially pure preparations of the individual isomers can be obtained.

If the chlorogenic acid is to be obtained in the form of a salt by the process according to the invention operations can be performed at the natural pH value of the aqueous plant extract. This has the advantage that the extracts freed from the chlorogenic acid salt remain unchanged and can be further utilized in foodstoff production.

However, in this embodiment of the process of the invention the separation capacity is lower than it is the case when free chlorogenic acid is prepared from an acidified extract. Accordingly in this embodiment the improvement in separation capacity with an increasing degree of cross-linkage of the gel used is of special importance.

DESCRIPTION OF THE PREFERRED EMBODIMENTS

Figure 1:
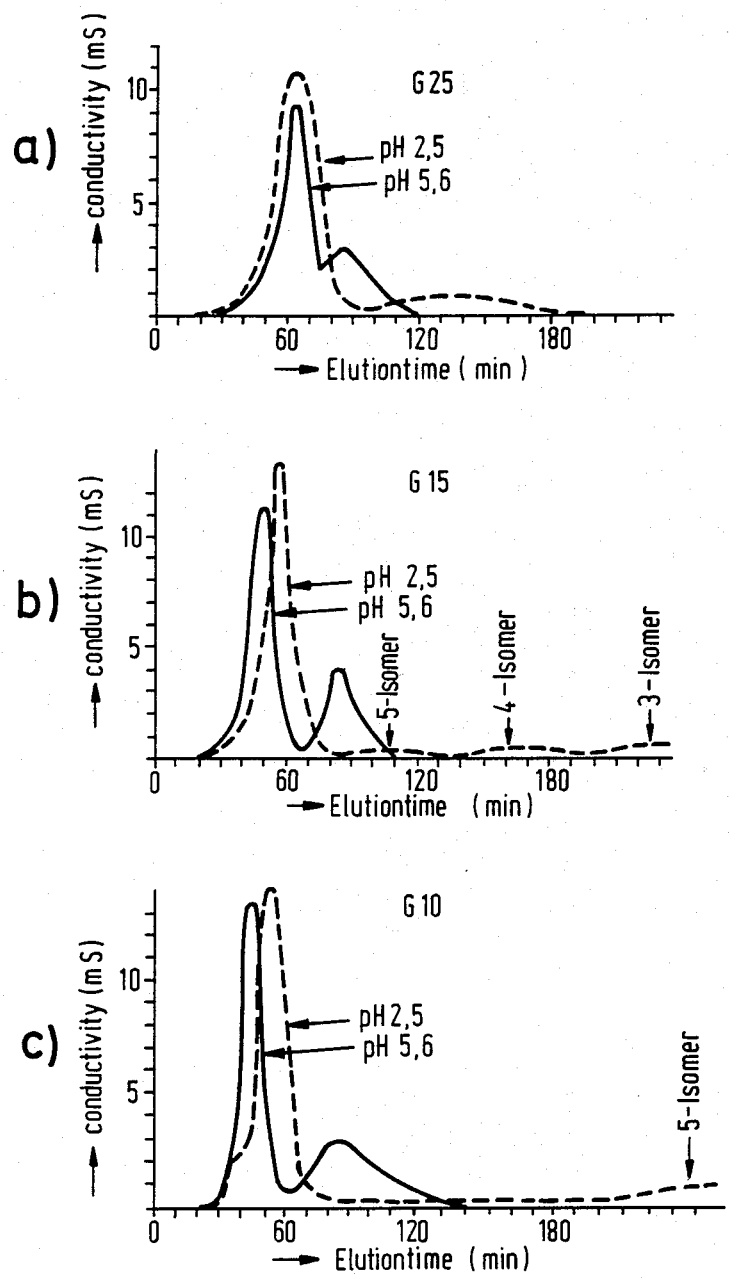
FIGS. 1A, 1B, and 1C show for a given length of column the separation characteristics are a function of both the pH of the plant extract to be separated and also of the degree of cross-linkage of the dextran gel used.

As shown in FIG. 1 for a given length of column the separation characteristics are a function of both the pH of the plant extract to be separated and also of the degree of cross-linkage of the dextran gel used. The chlorogenic acid was separated from decaffeinated raw coffee extract at the natural pH value of 5.6 as well as after acidification at pH 2.5 on the SEPHADEX-gels G 25, G 15 and G 10, whereby G 25 (see FIG. 1(a)) is cross-linked to the lowest and G 10 (see FIG. 1(c)) to the highest degree. All further conditions were kept constant, whereby the gel volume amounted to 150 ml, the flow rate to 150 ml/h and the temperature to 25° C. The eluate was monitored by means of a conductivity detector. Each column was loaded with 20 ml of an extract containing 20 g substance/100 ml based on dry weight.

As shown in FIG. 1(a) at pH 2.5 significant separation of chlorogenic acid is already obtained with SEPHADEX® G 25 which is cross-linked only to a low degree, while at pH 5.6 the peaks are still overlapping. In contrast nearly complete separation of chlorogenic acid from the other components is obtained also with the non-acidified extract if the more cross-linked G 15 is used (see FIG. 1(b)). If SEPHADEX® G 10 (see FIG. 1(c)) is used the basis of the chlorogenic acid peak is also broadened in the case of the non-acidified extract because of the beginning differentiation of the isomers.

Accordingly, with pH values above 2.8 such as are usually obtained in the preparation of aqueous plant extracts, use is preferably made of more cross-linked gels such as, for example, SEPHADEX® G 15, and even more cross-linked gels.

Of course the separation capacity when preparing chlorogenic acid salts from plant extracts with pH values above 2.8 may also or additionally be improved by increasing the column length.

The chlorogenic acid and its isomers may be analyzed in the individual eluate fractions by high pressure liquid chromatography (HPLC). In this way it is possible to determine for a particular column material and a given column length which eluate fractions contain the chlorogenic acid and to what extent the first efflux containing the accompanying substances must be separated. The chlorogenic acid can then be isolated in the usual manner from the eluate fractions in which it is contained, particularly under careful conditions as for example by freeze drying and can be obtained as solid substance. The fractions containing the accompanying substances may be treated accordingly to obtain a plant extract which is free from chlorogenic acid.

Plant raw materials containing chlorogenic acid in an adequate concentration are suitable as starting material. The following table shows the chlorogenic acid contents of various plant materials; the quantitative analysis was conducted with HPLC.

TABLE 1

| Plant material | Chlorogenic acid (% in dry material) |
|---|---|
| Green coffee beans | 5.0 |
| Bilberry leaves | 3.8 |
| Mate tea | 3.7 |

TABLE 1-continued

| Plant material | Chlorogenic acid (% in dry material) |
|---|---|
| Juniper leaves | 2.4 |
| Virginia Tobacco leaves | 1.4 |
| Whitetorn leaves | 0.6 |
| Maple leaves | 0.3 |
| Honeysuckle leaves | 1.4 |
| Honeysuckle fruits | 5.0 |
| Mahonia fruits | 1.6 |
| Unripe apples | 0.5 |

The process according to the invention offers a number of advantages over the prior art process. The process is substantially simpler, since it requires less process steps and only low apparatus expenditure. A particularly important feature is that the chlorogenic acid contained in the plant raw material can be substantially completely isolated and obtained. Another important feature is that the process is not limited to caffeine-containing starting material such as green coffee beans, but that other more inexpensive raw materials can also be used.

The process can be performed semi-continuously, since clearly the separating properties of the molecular sieve remain preserved for a very long time. For example, a column filled with cross-linked dextran showed reproducible properties, unchanged even after 100 runs. Each run comprises
- Application of the extract
- Elution of the accompanying substances,
- Elution of chlorogenic acid and
- Flushing.

The next run can immediately follow the flushing of the gel. If the column is contaminated the filling can be cleaned by very simple means. Suspended substances which impede throughflow can be rinsed away by stirring the gel in water. Dyestuffs retained by the gel can be removed in the throughflow with 0.2% caustic soda solution without the separating characteristics being influenced thereby. The following Examples will illustrate the invention in detail.

EXAMPLE 1

Preparation of free chlorogenic acid from bilberry leaves

To produce 175 ml gel, 35 g cross-linked dextran (SEPHADEX® 25 coarse) was swollen overnight with an excess of water. The resulting gel was transferred to a column and fixed between two adapters.

50 g bilberry leaves (Country of origin USSR) was extracted with 500 ml demineralized water at 80° C. The diluted extract was filtered and concentrated to 25 ml. in vacuo. It contained 1.1 g chlorogenic acid and 9.0 g other extract components. The pH of the extract was changed from 3.8 to 2.0 with 1.25 ml 37% hydrochloride acid. The solution was then pumped by a hose pump onto the separating column and then eluted with water at a constant flow rate of 100 ml/h. The eluate was separated into fractions of 25 ml, using a fraction collector.

Figure 2:
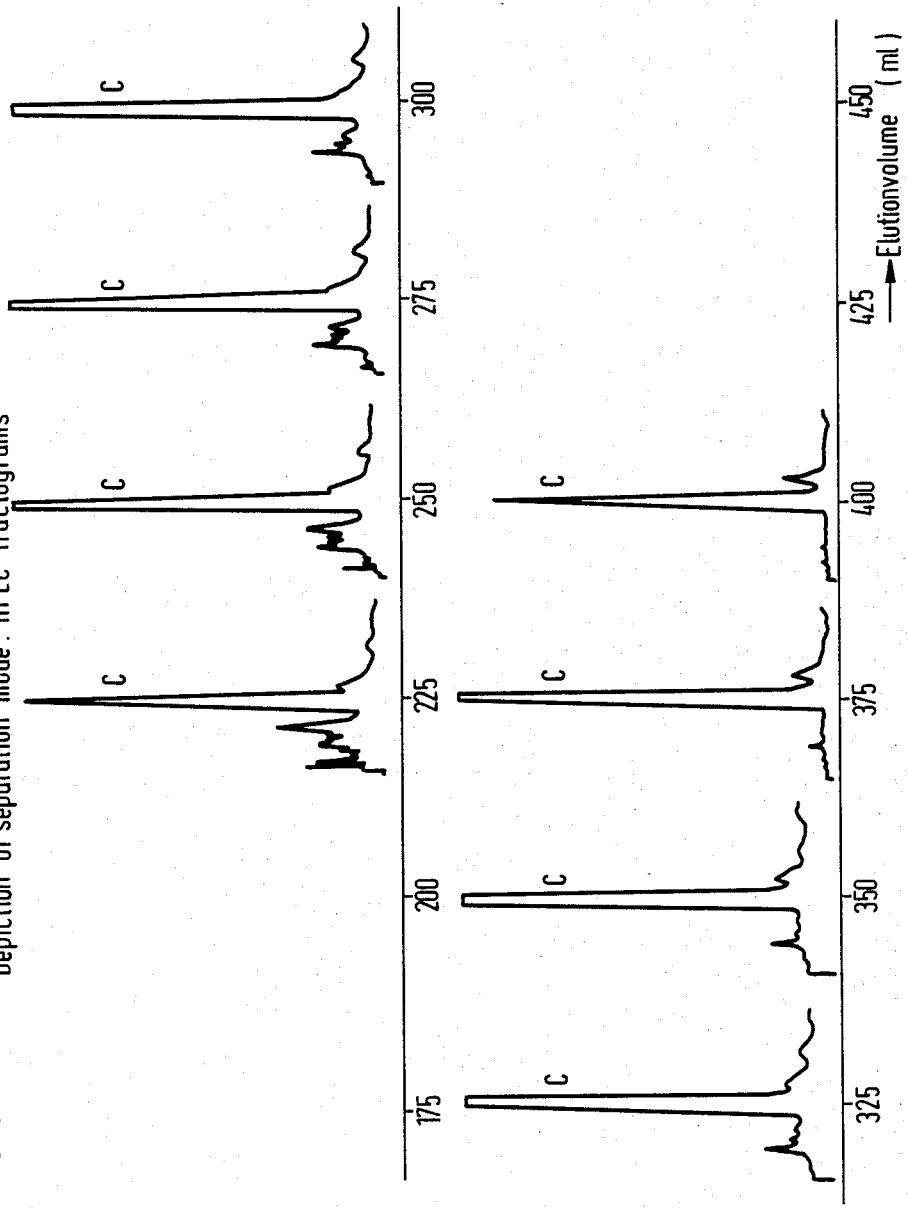
FIG. 2 shows the HPLC fractograms in dependence on the elution volume.

The chlorogenic acid content in the fractions was determined by HPLC. FIG. 2 shows the HPLC fractograms in dependence on the elution volume. As can be seen the fractions contain no chlorogenic acid up to an elution volume of 200 ml.

In the separation conditions selected, the chlorogenic acid is present in the elution volume between 200 and 425 ml. The selected fractions were combined, concentrated in vacuo and then freeze-dried. After the dissolution of pre-defined quantities in water, the chlorogenic acid content of the dry substances obtained was determined by HPLC in comparison with a standard.

Table 2 shows the quantities of dry substances obtained and the chlorogenic acid contents determined therein.

TABLE 2

| Elution volume (ml) | Dry substance (mg) | Chlorogenic acid (%) |
|---|---|---|
| 200–250 | 670 | 40.9 |
| 250–300 | 575 | 64.0 |
| 300–350 | 345 | 78.1 |

It can be seen from above table that the preparations are still contaminated to a varying extent with accompanying substances. An examination of the HPLC peak images shows this also.

The dry substances containing the chlorogenic acid were again dissolved in 25 ml water resulting in a pH of 2.3 and purified with 150 m gel (SEPHADEX® G 15).

The procedure was similar to the aforedescribed separation. In the second column the chlorogenic acid was contained in the elution volume between 650 and 1150 ml. In this case also selected fractions were combined, concentrated in vacuo and then freeze-dried. The dry preparations were analyzed for purity in the manner disclosed hereinbefore. The results are shown in Table 3.

TABLE 3

| Elution volume (ml) | Dry substance (mg) | Chlorgenic acid (%) |
|---|---|---|
| 650–775 | 400 | 81.5 |
| 775–900 | 300 | 94.5 |
| 900–1025 | 210 | 92.2 |
| 1025–1150 | 85 | 85.0 |

These figures show that the chlorogenic acid was obtained with a degree of purity of over 94% even without further recrystallization.

Figure 3:
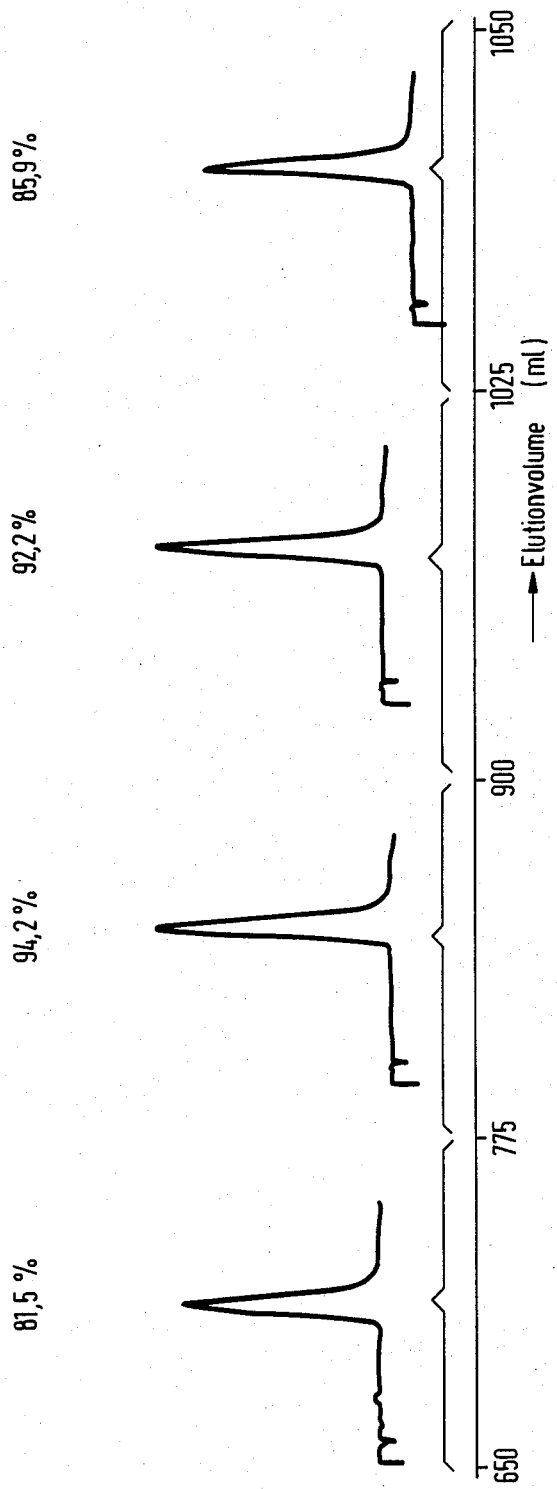
FIG. 3 shows the HPLC fractograms of the dry preparations produced from different elution volumes.

FIG. 3 shows the HPLC fractograms of the dry preparations produced from different elution volumes. The HPLC peak images indicate the purity obtained in the chlorogenic acid preparations thus produced.

EXAMPLE 2

Processing variants

Higher degrees of purity can be obtained even in the first step with columns of suitable size, but the appropriate procedure must be selected in each individual case. The significant feature is the chlorogenic acid content in the starting material. If the portion of chlorogenic acid in the dry extract is lower than 10% it makes better sense to operate with two separating columns. Here it is not necessary to concentrate the chlorogenic acid solution between two column passages. The most effective procedure is as follows:

The plant extract is passed through the first column (e.g. SEPHADEX® G 25 coarse) as an approximately 25% solution. The first eluate fractions containing the accompanying substances are cut out. Only when the chlorogenic acid has reached the end of the first column the eluate is fed directly onto the second column (e.g. SEPHADEX® G 15). This procedure prevents the second column used for purifying the chlorogenic acid from being loaded with the main portion of the accompanying substances.

EXAMPLE 3

Separation of a chlorogenic acid isomer mixture

For this experiment two separating columns were connected in series—one column with 175 ml SEPHADEX® G 25 coarse and one with 150 ml SEPHADEX® G 15. 1.6 g chlorogenic acid—isomer mixture were dissolved in 10 ml $H_2O$ at 40° C. and the acid solution was pressed as a starting zone into the separating system by a hose pump. Elution was performed with water at a flow rate of 75 ml/h. The emerging eluate was divided into 25 ml fractions and analyzed for chlorogenic acid by the HPLC method.

Figure 4:
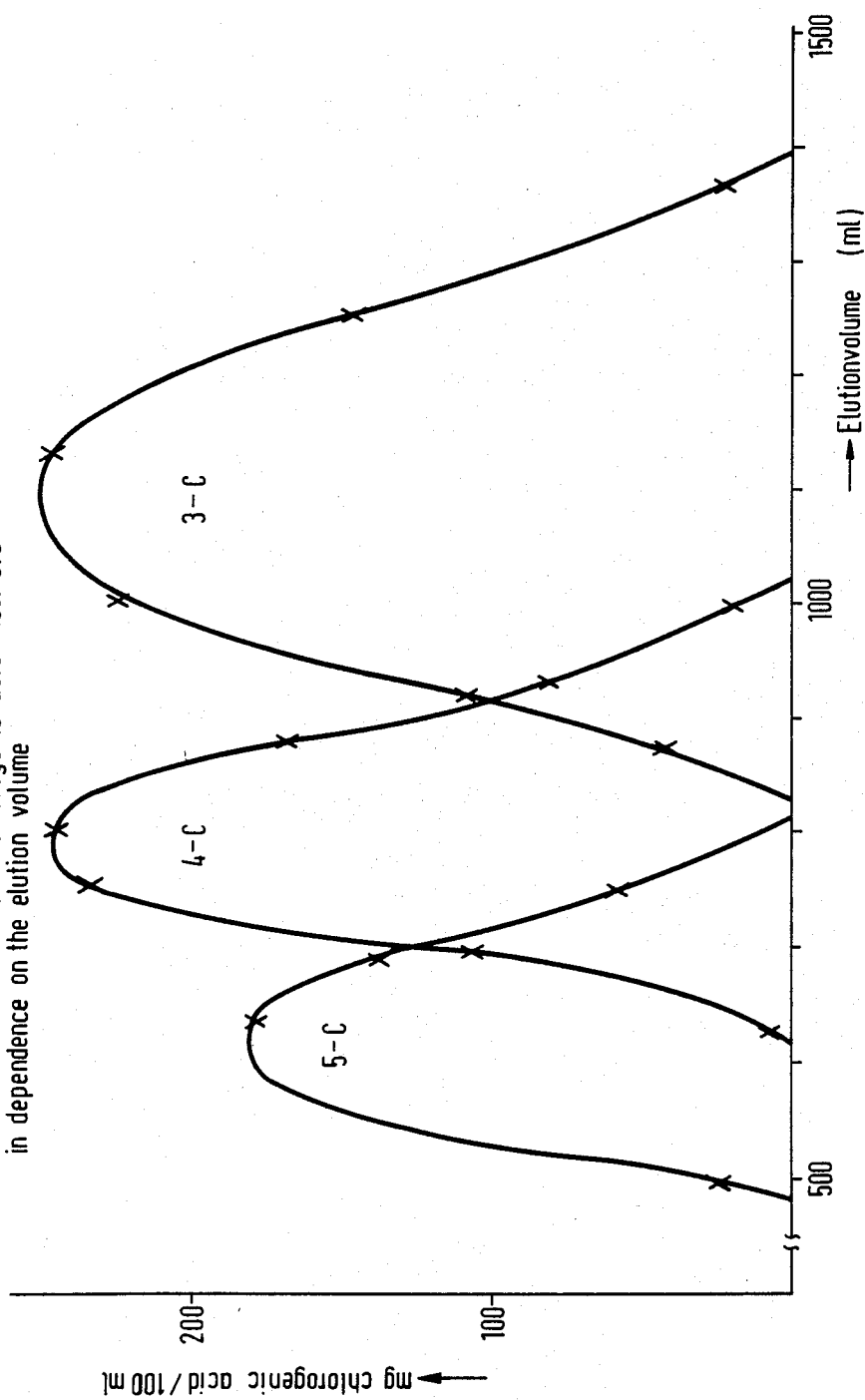
FIG. 4 shows the concentrations of the chlorogenic acid in dependence on the elution volume.

FIG. 4 shows the concentrations of the chlorogenic acid in dependence on the elution volume. A distinct separation into three chlorogenic acid isomers can be recognized. The distance of the chlorogenic acid isomer peaks can be increased by increasing the length of the separating column.

EXAMPLE 4

Preparation of chlorogenic acid in the form of a salt from raw coffee without pH correction.

100 g of decaffeinated raw coffee (country of origin: Columbia) was extracted with 300 ml demineralized water at 80° C. The pH of the extract was 5.6. The solution was subsequently concentrated to 50 ml. The extract concentration was 22.5 g dry substance 100 ml. Of these solutions 20 ml were pumped by a hose pump onto a column containing 50 ml gel (SEPHADEX® G 15).

The column was eluted with water at a temperature of 65° C. and at a flow rate of 300 ml/h. The eluate was gathered in 25 ml fractions and the chlorogenic acid content of the fractions was determined by HPLC.

The results are shown in Table 4.

TABLE 4

| Elution volume (ml) | Dry substance (g) | Chlorogenic acid (%) |
| --- | --- | --- |
| 25–150 | 3.17 | 0 |
| 150–225 | 1.30 | 70.7 |

As can be seen from table 4 the fractions contained no chlorogenic acid up to an elution volume of 150 ml. In the elution volume between 150 and 225 ml chlorogenic acid (substantially in the form of k-salt) was obtained with a purity of 70.7% even in the first run.

The yield was 97.9%, based on the chlorogenic acid content of the dry substance used.

I claim:

1. A process for separation and production of 3-, 4-, and 5-chlorogenic acid by extraction of plant raw materials in water comprising passing a water extract from plant raw material containing chlorogenic acid through a chromatography column containing crosslinked dextran whereby the chlorogenic acid is separated from accompanying substances by gel permeation chromatography on said cross-linked dextran and eluting said chlorogenic acid with water as elution medium to obtain a purity of greater than 70.7% in commercial scale amounts.

2. A process according to claim 1, in which the purity obtained is greater than 94% in commercial scale amounts.

3. Process according to claim 1, in that gel permeation chromatography is performed on at least two dextran gels of different degrees of cross-linkages, the first gel having the lower degree of cross-linkages, the first gel having the lower degree of cross-linkage and that part of the eluate of the first gel which contains the chlorogenic acid then being fed onto the next gel.

4. Process according to claim 3, in which the purity obtained is greater than 94% in commercial scale amounts.

5. Process according to claim 1 or 3 for the preparation of isomeric 5-, 4- and 3-chlorogenic acids having a last stage in that when gel permeation chromatography is performed, in the last stage a long enough column is used, from which the isomeric 5-, 4- and 3-chlorogenic acid are eluted in succession, the eluates being gathered separately.

6. Process according to claim 5, in which the purity obtained is greater than 94% in commercial scale amounts.

7. A process for the quantitative separation and production of 3-, 4- and 5-chlorogenic acid by extraction of plant raw materials comprising passing a water extract from plant raw material containing chlorogenic acid having a pH that has been adjusted to a range of about 2.0 to about 2.8 through a chromatography column containing cross-linked dextran whereby the chlorogenic acid is separated from the accompanying substances by gel permeation chromatography on a cross-linked dextran and eluting said chlorogenic acid on an elution medium consisting essentially of water and recovering chlorogenic acid at a purity of greater than 70.7% in commercial scale amounts.

8. A process according to claim 7, in which the purity obtained is greater than 94% in commercial scale amounts.

* * * * *